(12) United States Patent
Duval et al.

(10) Patent No.: US 11,744,453 B2
(45) Date of Patent: Sep. 5, 2023

(54) METHODS AND APPARATUS TO DETECT BLEEDING VESSELS

(71) Applicant: Boston Scientific Scimed, Inc., Maple Grove, MN (US)

(72) Inventors: George Wilfred Duval, Sudbury, MA (US); Karim Tarabein, Shaker Heights, OH (US); Steven Glaser, Charlotte, NC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 417 days.

(21) Appl. No.: 16/899,085

(22) Filed: Jun. 11, 2020

(65) Prior Publication Data
US 2020/0394792 A1    Dec. 17, 2020

Related U.S. Application Data

(60) Provisional application No. 62/860,962, filed on Jun. 13, 2019.

(51) Int. Cl.
*A61B 1/273* (2006.01)
*A61B 1/00* (2006.01)
(Continued)

(52) U.S. Cl.
CPC ...... *A61B 1/2736* (2013.01); *A61B 1/000094* (2022.02); *A61B 1/000095* (2022.02);
(Continued)

(58) Field of Classification Search
CPC ............ G06T 7/0012; G06T 5/40; G06T 2207/10024; G06T 2207/10068;
(Continued)

(56) References Cited

U.S. PATENT DOCUMENTS

2010/0222671 A1    9/2010    Cohen et al.
2011/0319752 A1    12/2011   Steinberg et al.
(Continued)

FOREIGN PATENT DOCUMENTS

| JP | WO-2013/145407 A1 | * | 11/2012 | ......... A61B 1/00009 |
| WO | WO-2004/005895 A1 | * | 1/2004 | ......... G01N 21/6456 |
| WO | WO 2004/005895 A1 | | 1/2004 | |

OTHER PUBLICATIONS

International Search Report, dated Aug. 31, 2021, in related application PCT/US2020/037244 (4 pages).

*Primary Examiner* — Gandhi Thirugnanam
(74) *Attorney, Agent, or Firm* — Bookoff McAndrews PLLC

(57) ABSTRACT

According to one aspect, a processor device in communication with an endoscopic device obtains a spectrum image of bleeding in an upper gastrointestinal (GI) area of a patient. A filter is applied to the spectrum image to generate a pre-enhanced image. The filter enhances the spectrum image at one or more light wavelengths in the light spectrum. The pre-enhanced image is analyzed to identify an area of interest that represents a portion of the upper GI area with an active bleed. A contrast enhancement technique is applied to the area of interest in the pre-enhanced image to generate an enhanced contrast image. Spatial filters are applied to the enhanced contrast image to produce a final colorized image with defined blood vessels in the upper GI area of the patient.

17 Claims, 11 Drawing Sheets

(51) Int. Cl.
*G06T 5/40* (2006.01)
*G06T 7/00* (2017.01)

(52) U.S. Cl.
CPC ............ *A61B 1/00186* (2013.01); *G06T 5/40* (2013.01); *G06T 7/0012* (2013.01); *G06T 2207/10024* (2013.01); *G06T 2207/10068* (2013.01); *G06T 2207/20024* (2013.01); *G06T 2207/30092* (2013.01)

(58) Field of Classification Search
CPC . G06T 2207/20024; G06T 2207/30092; G06T 2207/10; A61B 1/00186; A61B 1/2736; A61B 1/00002; A61B 1/00004; A61B 1/00009; A61B 1/000094; A61B 1/000095; A61B 1/00163; A61B 1/273; A61B 1/044; A61B 1/04; A61B 1/046; A61B 1/06; A61B 1/0638
See application file for complete search history.

(56) References Cited

U.S. PATENT DOCUMENTS

| | | | |
|---|---|---|---|
| 2015/0379712 A1* | 12/2015 | Guissin | ................. A61B 5/725 382/128 |
| 2018/0064320 A1 | 3/2018 | Chiba | |
| 2020/0394792 A1* | 12/2020 | Duval | ................ A61B 1/00186 |

* cited by examiner

METHODS AND APPARATUS TO DETECT BLEEDING VESSELS

CROSS-REFERENCE TO RELATED APPLICATIONS

This application claims the benefit of priority from U.S. Provisional Application No. 62/860,962, filed Jun. 13, 2019, which is incorporated by reference herein in its entirety.

TECHNICAL FIELD

Examples of the present disclosure relate to, among other things, a medical system and related methods. More specifically, this disclosure relates to an endoscopy system with capabilities to detect bleeding vessels in a monochromatic field of view.

BACKGROUND

Endoscopic procedures may include visualization of a target area in a subject's body proximate a distal end of an endoscope inserted into the subject's body. One form of visualization may include visual imaging of the target area. Some targeted areas for visualization in the body, such as the upper gastrointestinal (GI) tract, may have an occurrence of active tissue bleeding. In some examples, determining the source of the bleeding (e.g., in upper GI bleeding (UGIB)) is critical in not only the health of the patient but also in mitigating potential re-admission of the patient for treatment.

SUMMARY

Examples of the present disclosure relate to, among other things, a medical system with capabilities to detect bleeding vessels in a monochromatic field of view, and related methods. Each of the examples disclosed herein may include one or more of the features described in connection with any of the other disclosed examples.

According to one aspect, a method is provided for enhancing medical images. The method comprises obtaining, at a processor device in communication with an endoscopic device, a spectrum image of bleeding in an upper gastrointestinal (GI) area of a patient A filter is applied to the spectrum image to generate a pre-enhanced image. The filter enhances the spectrum image at one or more light wavelengths in the light spectrum. The pre-enhanced image is analyzed to identify an area of interest. The area of interest represents a portion of the upper GI area with an active bleed. A contrast enhancement technique is applied to the area of interest in the pre-enhanced image to generate an enhanced contrast image. Spatial filters are applied to the enhanced contrast image to produce a final colorized image with defined blood vessels in the upper GI area of the patient.

The method may include one or more operations below. A filter may be applied to the spectrum image at a light wavelength at which a light absorption rate of oxygenated hemoglobin differs from a light absorption rate of deoxygenated hemoglobin. The filter may be applied to the spectrum image at one or more light wavelengths between 490 nanometers and 640 nanometers. The filter may be applied to the spectrum image using a red-green-blue (RGB) color filter. The contrast enhancement techniques may apply one of a Bayesian classifier enhancement technique, a histogram contrast algorithm, or a red-balance hue filter (R-filter) to the area of interest. Applying the R-filter to the area of interest may comprise converting the area of interest to grayscale using the R-filter.

According to one aspect, the method may also include one or more operations below. The filter may be applied to the spectrum image to generate the pre-enhanced image with an area of interest more visually enhanced than the spectrum image. The contrast enhancement techniques may be applied to the area of interest to generate the enhanced contrast image with the area of interest more visually enhanced than the pre-enhanced image. The spatial filters may be applied to the enhanced contrast image to produce the final colorized image that represents a recolorization of the enhanced contrast image. The contrast enhancement technique may be applied during real time imaging of the patient and/or during post-processing after the spectrum image is obtained from the patient. The pre-enhanced image may be analyzed to identify the area of interest that is a narrow field of visualization of the pre-enhanced image.

According to one aspect, a non-transitory computer readable medium is provided that stores instructions. When the instructions are executed, the instructions cause one or more processors of a computer system to perform operations. A spectrum image of bleeding in an upper gastrointestinal (GI) area of a patient is obtained from an endoscopic device. A filter is applied to the spectrum image to generate a pre-enhanced image. The filter enhances the spectrum image at one or more light wavelengths in the light spectrum. The pre-enhanced image is analyzed to identify an area of interest. The area of interest represents a portion of the upper GI area with an active bleed. A contrast enhancement technique is applied to the area of interest in the pre-enhanced image to generate an enhanced contrast image. Spatial filters are applied to the enhanced contrast image to produce a final colorized image with defined blood vessels in the upper GI area of the patient.

The instructions of the computer readable medium may cause the processor to perform other operations. A filter may be applied to the spectrum image at a light wavelength at which a light absorption rate of oxygenated hemoglobin differs from a light absorption rate of deoxygenated hemoglobin. The filter may be applied to the spectrum image atone or more light wavelengths between 490 nanometers and 640 nanometers. The filter may be applied to the spectrum image using a red-green-blue (RGB) color filter. The contrast enhancement techniques may apply one of a Bayesian classifier enhancement technique, a histogram contrast algorithm, or a red-balance hue filter (R-filter) to the area of interest. Applying the R-filter to the area of interest may comprise converting the area of interest to grayscale using the R-filter.

According to one aspect, a computer device is provided for enhancing medical images. The computer device comprises an interface unit, a memory storing instructions, and one or more processors configured to perform operations. A spectrum image of bleeding in an upper gastrointestinal (GI) area of a patient is obtained from an endoscopic device. A filter is applied to the spectrum image to generate a pre-enhanced image. The filter enhances the spectrum image atone or more light wavelengths in the light spectrum. The pre-enhanced image is analyzed to identify an area of interest. The area of interest represents a portion of the upper GI area with an active bleed. A contrast enhancement technique is applied to the area of interest in the pre-enhanced image to generate an enhanced contrast image. Spatial filters are applied to the enhanced contrast image to produce a final colorized image with defined blood vessels in the upper GI area of the patient.

The one or more processors of the computer device may perform other operations. A filter may be applied to the spectrum image at a light wavelength at which a light absorption rate of oxygenated hemoglobin differs from a light absorption rate of deoxygenated hemoglobin. The filter may be applied to the spectrum image at one or more light wavelengths between 490 nanometers and 640 nanometers. The filter may be applied to the spectrum image using a red-green-blue (RGB) color filter. The contrast enhancement techniques may apply one of a Bayesian classifier enhancement technique, a histogram contrast algorithm, or a red-balance hue filter (R-filter) to the area of interest Applying the R-filter to the area of interest may comprise converting the area of interest to grayscale using the R-filter.

It may be understood that both the foregoing general description and the following detailed description are exemplary and explanatory only and are not restrictive of the claimed features. As used herein, the terms "comprises," "comprising," "includes," "including," or any other variation thereof, are intended to cover a non-exclusive inclusion, such that a process, method, article, or apparatus that comprises a list of elements does not have only those elements, but may have other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure, and together with the description, serve to explain the principles of the disclosure.

DETAILED DESCRIPTION

Examples of the present disclosure are drawn to medical systems with capabilities to detect bleeding vessels in a monochromatic field of view. These capabilities may enable the diagnosis of a patient with an active bleed for improved therapy to reduce the risk for re-bleeding and to provide a more effective hemostasis therapy. Additionally, the techniques described herein may enable identification of non-bleeding visible vessels (NBVV) in the upper gastrointestinal (GI) region of a patient that have potential for re-bleeding events. In general, the techniques described herein utilize the hemoglobin oxygenation/de-oxygenation optical spectrum to improve contrast in a monochromatic field of view (e.g., pooling of blood). These contrast enhancements can greatly impact patient care and reduce re-bleed and readmission of active bleeders/NBVV in upper GI bleeding cases by revealing bleeding vessels in pools of blood or just under a surface of a mucosa layer in a patient.

Figure 1:
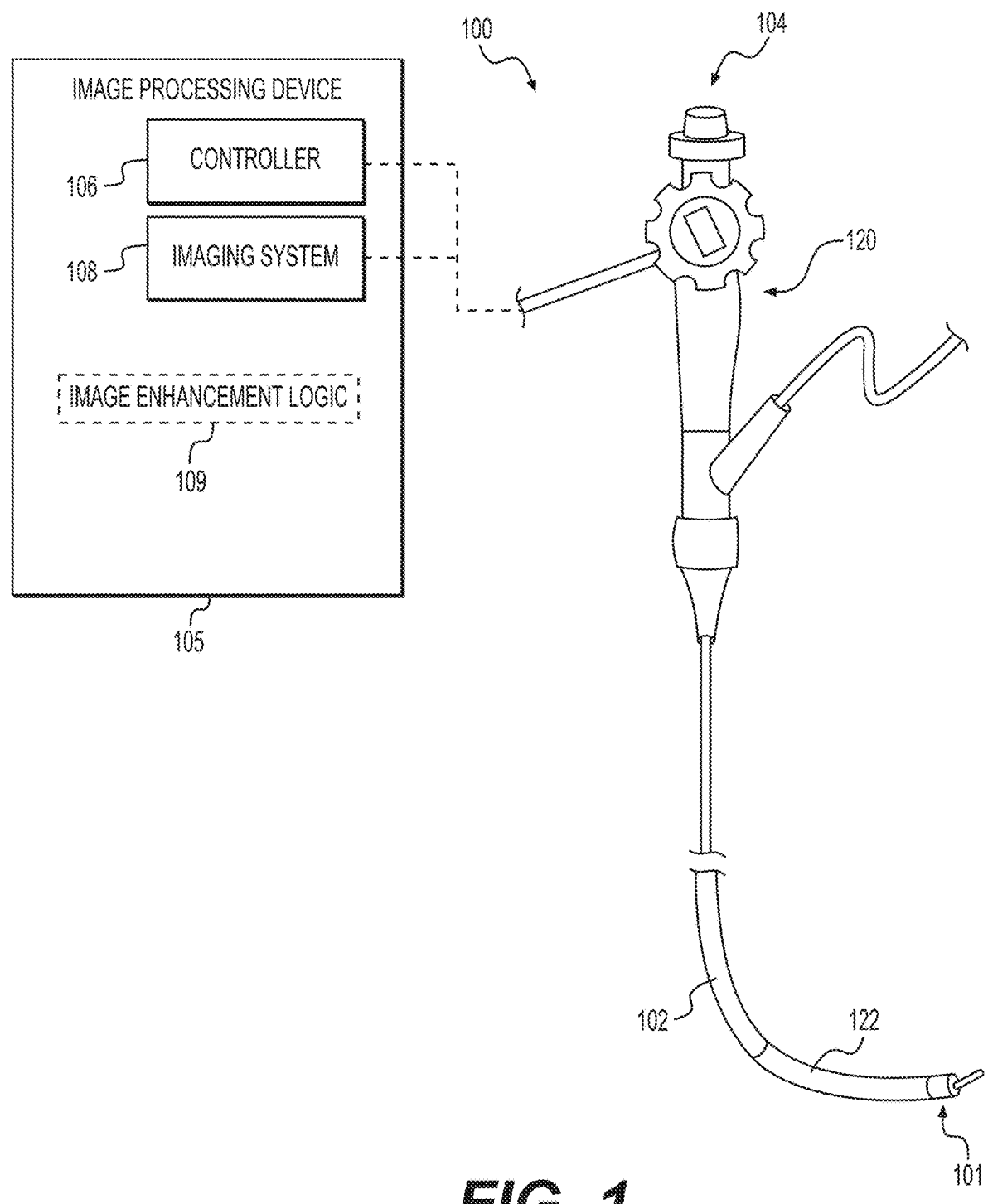
FIG. 1 illustrates an endoscopy system, according to an exemplary embodiment of the present disclosure.

An exemplary endoscopy system 100 is shown in FIG. 1. Endoscopy system 100 may include an endoscope 104. Endoscope 104 may include a handle assembly 120 and a flexible tubular shaft 102. The flexibility of shaft 102 may be sufficient to allow shaft 102 to bend in order to facilitate navigation of shaft 102 through a subject's tortuous anatomical passages. Shaft 102 may terminate at a distal tip 101. Shaft 102 may include an articulation section 122 for deflecting distal tip 101 in up, down, left, and/or right directions. In one example, articulation section 122 may provide for full retroflexion (e.g., rotation of distal tip 101 through an arc of 180 degrees) or only partial retroflexion (e.g., rotation of distal tip 101 through an arc of less than 180 degrees). Endoscope 104 also may include one or more lumens extending therethrough, and one or more openings in communication with the one or more lumens. For example, the one or more lumens may extend through handle assembly 120 and shaft 102, and the one or more openings may be on handle assembly 120 and distal tip 101.

One or more auxiliary devices may be operatively coupled to endoscope 104. Exemplary auxiliary devices may include an image processing device 105. The image processing device 105 may include, for example, a controller 106, an imaging system 108, and image enhancement logic 109 stored in memory (not shown in FIG. 1) of the image processing device 105. The image enhancement logic 109 is configured to enhance the contrast of images to detect bleeding vessels in a monochromatic field of view, according to exemplary techniques described herein. The controller 106 of the image processing device 105 may include, for example, any electronic device capable of receiving, storing, processing, generating, and/or transmitting data according to instructions given by one or more programs. Controller 106 may be operatively coupled to, or part of, one or more of the endoscope 104 and the other auxiliary devices, to control one or more aspects of their operation. Although illustrated as an integral component, it is understood that all or any combination, or elements of, the image processing device 105 may be separate components, operably coupled to each other and/or the endoscope 104 via wired and/or wireless connections.

The imaging system 108 may include imaging electronics to, for example, process signals received from an image sensor in endoscope 104, send signals for controlling an image sensor, adjust illumination levels of areas being viewed by the image sensor, and/or facilitate the display of image sensor data on a display. The imaging system is configured to capture an image of a region within a patient's body, for example, bleeding vessels in the upper GI region of a patient. In one example, the imaging system 108 may be a camera system or other image capturing system configured to utilize the endoscope 104 to capture the image of a region within the patient's body.

Other auxiliary devices not shown in FIG. 1 may include a power supply, a fluid supply assembly, a vacuum source, and a display. The power supply may be any suitable power source, and associated connectors (e.g., electrically-conductive wires), for supplying electronic components in the auxiliary devices and endoscope 104 with electrical power.

The fluid supply assembly may include a reservoir, a medical irrigation bag, a pump, and any suitable connectors (e.g., tubing for fluidly coupling fluid supply and endoscope 104). The pump may supply a flow of pressurized fluid to one or more of the lumens in endoscope 104, and the pressurized fluid flow may be emitted from distal tip 101 and/or used to inflate expandable components present at distal tip 101. The vacuum source may provide suction or vacuum pressure to one or more lumens of the endoscope, and thereby provide a suction force to draw material toward and/or into endoscope 104, and/or to deflate expandable components.

Although examples within this disclosure are described in connection with an endoscopy system, the disclosure is not so limited. Aspects of this disclosure may be used in any other medical system, including any system that requires visualization of internal anatomy.

Figure 2A:
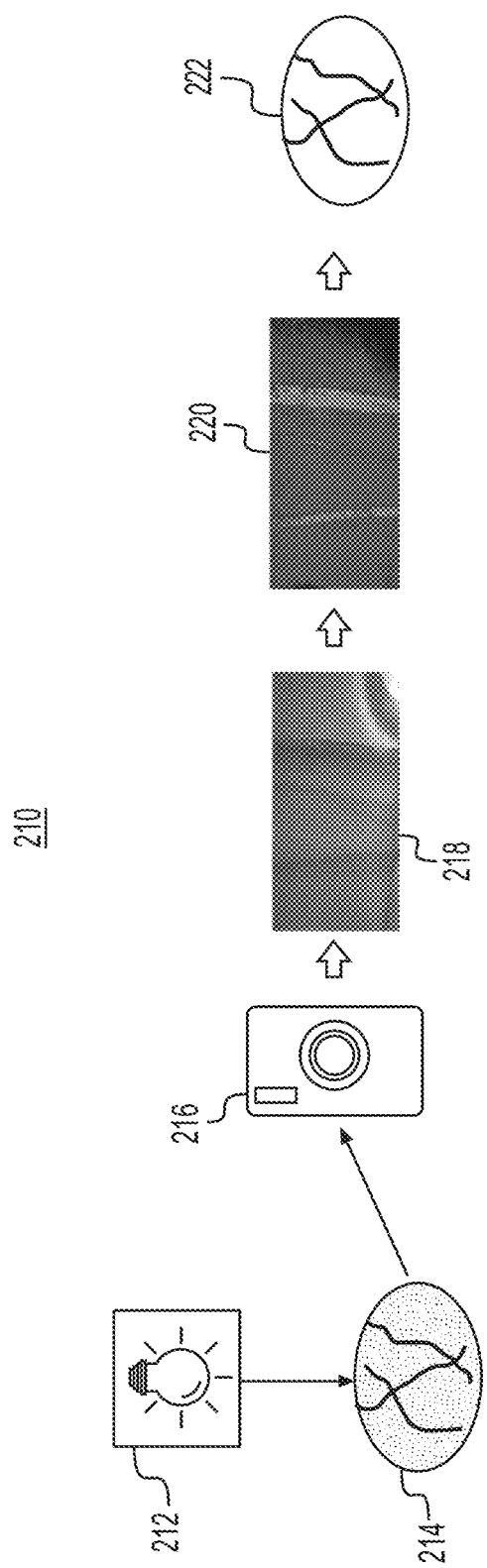
FIGS. 2a-2d illustrate image enhancement systems, according to exemplary aspects of the present disclosure.

Reference is now made to FIGS. 2a-2d, which show example image enhancement systems according to exemplary aspects of the present disclosure. FIG. 2a shows a first image enhancement system 210. The first image enhancement system 210 shows an illumination source 212, a spectrum image 214, a spectral imager 216, a pre-enhanced image 218, an enhanced contrast image 220, and a final colorized image 222. It should be appreciated that the operations of the illumination source 212 and of the spectrum imager 216, the filtering techniques, and image enhancement techniques described hereinafter may be executed by a computing device (e.g., the image processing device 105, described in connection with FIG. 1).

In general, the illumination source 212 is an illumination device configured to project full spectrum light onto a tissue area of interest of a patient via the endoscope 104. The illumination source 212 may utilize, for example, the one or more lumens extending through the handle assembly 120 and the shaft 102 of the endoscope 104, as described in connection with FIG. 1 above. For example, the illumination source 212 may be a light source external to the endoscope 104 that is configured to deliver illumination via the lumens (or other optical channels) to the distal tip 101 of the endoscope 104 for projection onto a tissue region of a patient. In another example, the illumination source 212 may be part of the endoscope 104 itself, for example, an illumination source at the distal tip 101 that is illuminated via a power supply external to the endoscope 104. In one example, the illumination source 212 in FIG. 2a is a light source configured to emit full spectrum light onto a tissue region, for example, wavelengths of light in the visible spectrum between 400 nanometers (nm) and 700 nm, though it should be appreciated that the illumination source may also be configured to emit light in the nonvisible spectrum (e.g., ultraviolet and/or infrared light) as needed.

After the illumination source 212 emits light onto a tissue region of the patient, the imaging system 108 (described in connection with FIG. 1) captures the spectrum image 214. As referenced herein, the term capture may mean, as an example, recording, storing in memory, and/or displaying data to a user. The spectrum image 214 represents a full spectrum standard image captured over the full visible light spectrum. In one example, the spectrum image 214 may represent upper GI bleeding (e.g., a pooling blood model with blood vessels). In one example, the spectrum image 214 may be a single image, a plurality of images, and/or a combination of images. If the bleeding is extensive, a viewer of the spectrum image 214 may not be able to discern the blood vessels that are causing the bleed, since, in this example, pooling of blood may obfuscate the location of the vessels in the spectrum image 214. The techniques described herein include processes by which the source of such bleeding may be identified through spectral analysis and enhanced contrast methods. This may improve the effectiveness of hemostasis therapeutic remedies and reduce readmissions of patients for active bleeds and non-bleeding visible vessels.

Figure 5A:
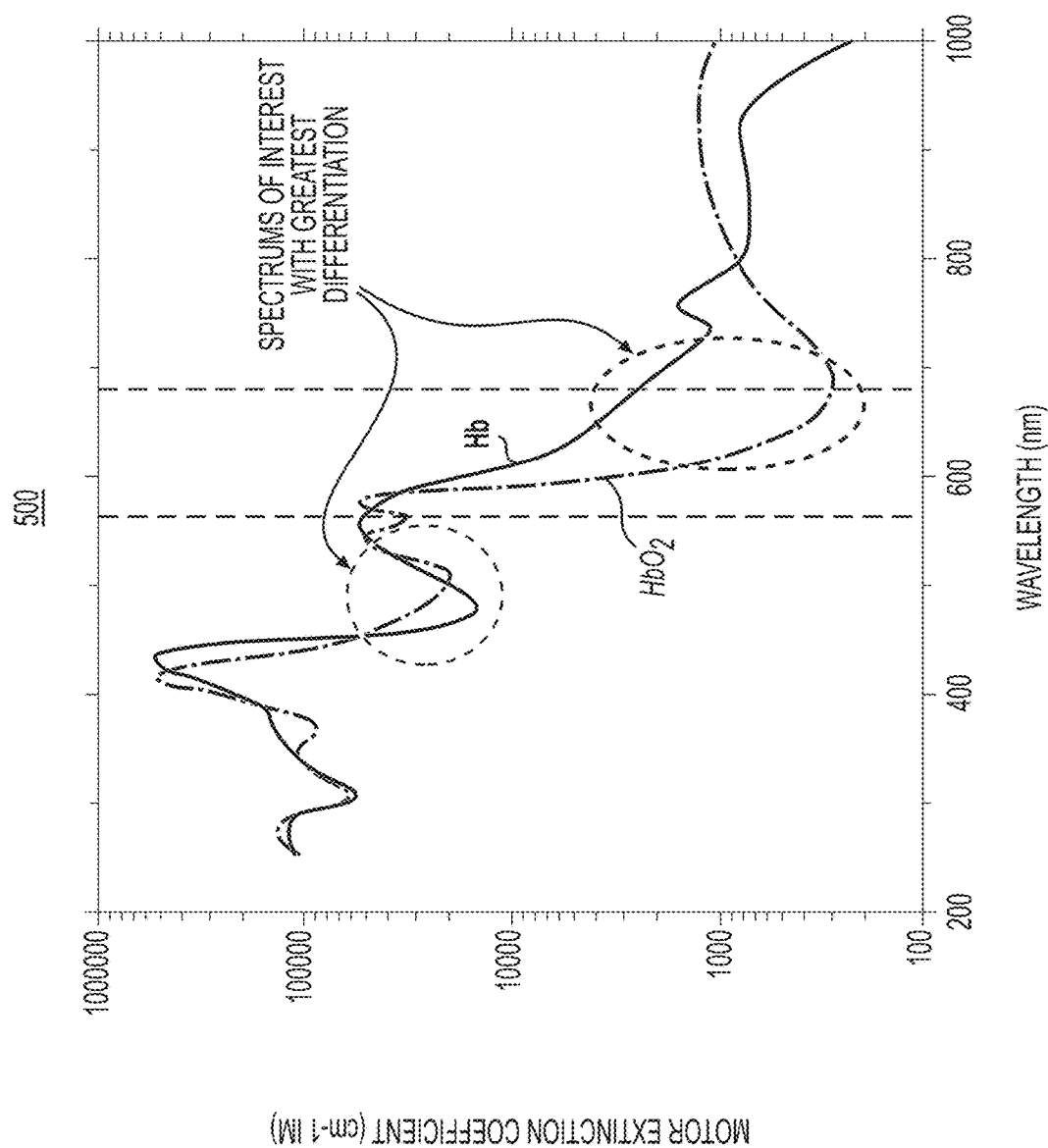
FIG. 5a illustrates an example graph depicting light absorption properties of hemoglobin, according to exemplary aspects of the present disclosure.

The spectral imager 216 is configured to apply one or more filters to the spectrum image 214. In embodiments, the spectral imager 216 applies the filters to enhance the spectrum image 214 at selected light wavelengths. In the example of an active upper GI bleeding event, described above, the spectral imager 216 applies to the spectrum image 214 filters to enhance light wavelength components of the spectrum image 214. These filters may be applied at selected light wavelengths such that bleeding vessels in the image are more visually enhanced after the filtering relative to the original spectrum image 214. In one example, the spectral imager 216 applies filters to the spectrum image 214 at light wavelengths at which a light absorption rate of oxygenated hemoglobin differs from a light absorption rate of deoxygenated hemoglobin. For example, pooling blood in an upper GI bleed may have a different percentage of oxygenated hemoglobin than the percentage of arterial or venous blood oxygenation. FIG. 5a illustrates an example graph 500 depicting light absorption properties of hemoglobin. Referring to FIG. 2a and FIG. 5a concurrently, the spectral imager 216 may focus on wavelengths that show the greatest differentiation in light absorption between oxygenated and deoxygenated hemoglobin. These wavelengths may be the most useful for the spectral imager 216 to enhance the bleeding vessels from a pool of blood in the spectrum image 214. For example, the spectral imager 216 may apply a filter to enhance light absorption in the spectrum image 214 at light wavelengths between about 490 nm and about 640 nm, and more specifically at about 490 nm, about 630 nm, and about 640 nm. In one example, the wavelengths may be selected automatically by an image capturing system, and in another example, the wavelengths may be selected automatically by a user.

For example, as shown in FIG. 5a, at a 490 nm wavelength, de-oxygenated hemoglobin has a known lower absorption factor than oxygenated hemoglobin (e.g., extrapolated from a Molar-Extinction Coefficient). At wavelengths in the 630 nm to 640 nm range, the relationship flips. That is, in the 630 nm to 640 nm wavelength range, oxygenated hemoglobin has a known lower absorption factor than de-oxygenated hemoglobin. In one example, as described by the techniques herein, the spectral imager 216 may apply a filter to enhance light absorption at wavelength between 630 nm and 640 nm to verify slope calculations during a Naïve Bayesian classification. In this wavelength window, de-oxygenated hemoglobin has a more gradual slope as well. Thus, by applying filter to enhance light absorption at wavelengths about 490 nm, 630 nm, and 640 nm, the techniques described herein enable differentiation in viewing oxygenated blood entering from a vessel and classifying de-oxygenated pooling blood. This is particularly useful in environments where pooling blood may have less oxygenated blood or may have oxygenated blood that dilutes pooling blood that is decreasing in oxygenated hemoglobin.

These wavelengths may show the greatest diversity in absorption with respect to oxygenated and deoxygenated hemoglobin, and thus may provide significant contrast enhancement opportunities for image differentiation of bleeding vessels in a pool of blood. It should be appreciated that the term "about" may be used to indicate a variation from a stated value, for example, a +/−10% variation from the stated value.

In one example, the illumination source 212 may be in the visible spectrum, and may include a standard halogen light projection, xenon light projection and/or a light emitting diode (LED). The spectral imager 216 may be any known or heretofore contemplated spectral imager, including a 1×1 millimeter red-green-blue imager, a 250×250 or 400×400 pixel array, an imager with sensitivity of 100 millivolts per lux seconds, etc.

After the spectral imager 216 applies the filters to the spectrum image 214, the spectral imager 216 generates a pre-enhanced image 218. The image processing device 105 may analyze the pre-enhanced image 218 to determine an area of interest in the pre-enhanced image 218. The area of interest may be a section of the pre-enhanced image 218 or the spectrum image 214 that is desired to be enhanced, and the area of interest may be selected by a user or automatically. For example, the area of interest may be a narrow field of visualization of the pre-enhanced image 218 or the spectrum image 214. In one embodiment, the area of interest may be an area of the pre-enhanced image 218 or the spectrum image 214 that represents bleeding vessels in an upper GI bleeding scenario). In general, the pre-enhanced image 218 shows a more visually enhanced area of interest relative to the spectrum image 214. For example, bleeding vessels in an active upper GI bleeding event may be more readily apparent in the pre-enhanced image 218 than the spectrum image 214. The pre-enhanced image 218 may be a false color image with three spectral filters (e.g., at 490 nm, 630 nm, and 640 nm).

After the pre-enhanced image 218 is generated, the system 210 may apply a contrast enhancement technique to further enhance an identified area of interest in the pre-enhanced image 218. For example, the pre-enhanced image 218 may show regions of interest, such as bleeding vessels, that are more visually enhanced relative to the spectrum image 214 but may not show further differentiations within the areas of interest. As a result, a contrast enhancement technique may be applied to the pre-enhanced image 218 to further visually enhance the area of interest, and thus generate an enhanced contrast image 220. In FIG. 2a, the enhanced contrast image 220 is generated by using a Naïve Bayesian classifier to further color the blood vessels in the area of interest in the pre-enhanced image 218. The Naïve Bayesian classifier is a supervised classifier. A supervised classifier is trained with a number of classes, each with user-selected spectra. With hyperspectral images, for example, a hypercube image is obtained. For every class of object in the scene, training samples are selected (e.g., manually or through a feature extraction based on the overlay of the three spectral filters). For each class and area of interest, a color can be assigned to it as a defining contrast. In one example, a supervised classifier can be trained to apply an artificial color where only pooling blood appears. The classifier can then be trained for enhancement with a different color for underlying vessels.

Figure 5B:
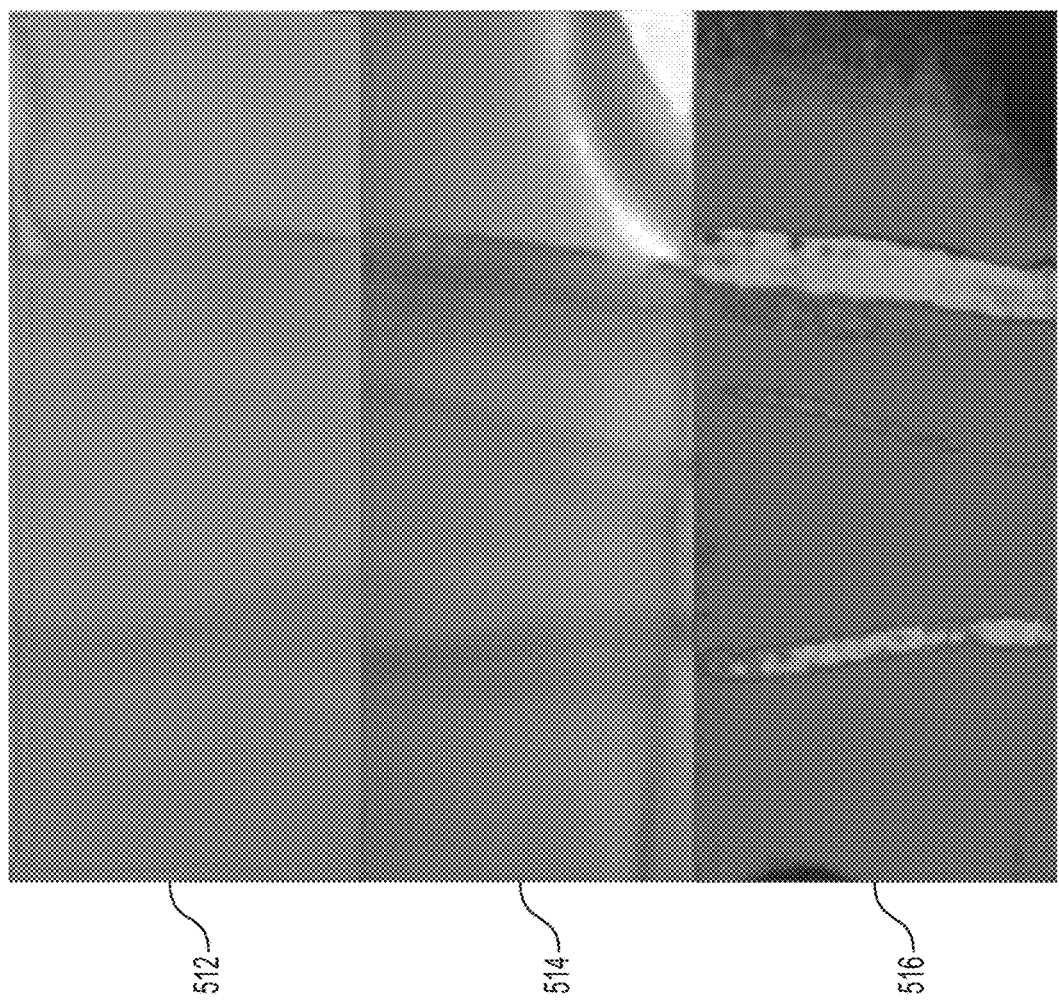
FIG. 5b shows example images, according to exemplary aspects of the present disclosure.

FIG. 5b shows example images 510. For example, FIG. 5b shows a red-green-blue image 512, a false color image with filters 514, and an image after Naïve Bayesian Classification 516. Each of the filtered images are provided in grey scale, and false colorization pallets are applied to each filtered image before overlaying to provide better contrasting when superimposing each image. A false color representation is a red-green-blue image, where the red, green, and blue channels are individual bands selected from a hypercube. For example, 490 nm, 630 nm, and 640 nm are selected for red, green, and blue colorization, respectively.

In one example, the pre-enhanced image 218 is falsely colorized due to the filtering at the spectral imager 216, and the enhanced contrast image 220 further colorizes the falsely colored pre-enhanced image 218 to generate the enhanced contrast image 220 (e.g., a Naïve Bayesian contrast image).

Figure 5C:
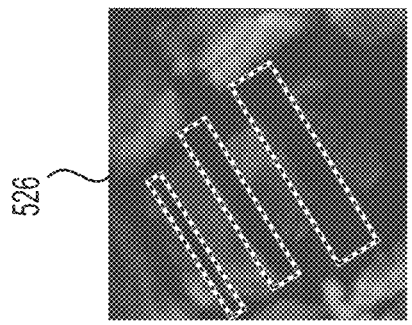
FIG. 5c shows other example images, according to exemplary aspects of the present disclosure.
Figure 5C:
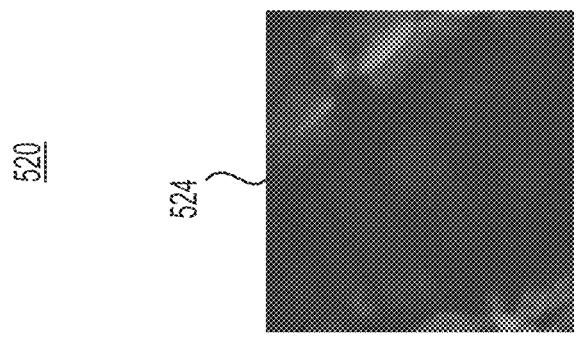
Figure 5C:
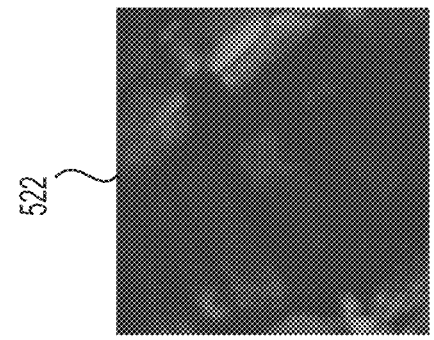

Returning to FIG. 2b, after the enhanced contrast image 220 is generated (e.g., by the image processing device 105), spatial filters are applied to the enhanced contrast image to generate the final colorized image 222. The final colorized image 222 represents a recolorization of the enhanced contrast image 220 through spatial filters to produce a final image with the blood vessels defined. In general, spatial filtering refers to pixel to pixel image processing for 2D images (not hybercubes). Examples of spatial filter includes averaging, smoothing, zero-padding, symmetrical, circular, low pass filtering, and high pass filtering. FIG. 5c shows example images 520. For example, the images 520 may include a first image 522 that is an original red-green-blue image, a second image 524 having a red (R) to gray scaled filter applied, and a third image 526 having a spatial filter applied. The spatial filter may be a simple weighted average filter that is applied after a gray scale conversion to show enhanced images.

Returning to FIG. 2a, the system 210 in FIG. 2a enables a viewer to identify active bleeding vessels in a tissue bleeding area (e.g., an upper GI bleeding event). The viewer can utilize the spectrum image 214 to navigate to an area of interest, and then utilize the pre-enhanced image 218, enhanced contrast image 220, and final colorized image 222 to clearly view the bleeding vessels in the area of interest. It should be appreciated that the techniques herein may be applicable for other bleeding events or tissue detection environments, and the upper GI bleeding scenario described herein is merely an example.

Figure 2B:
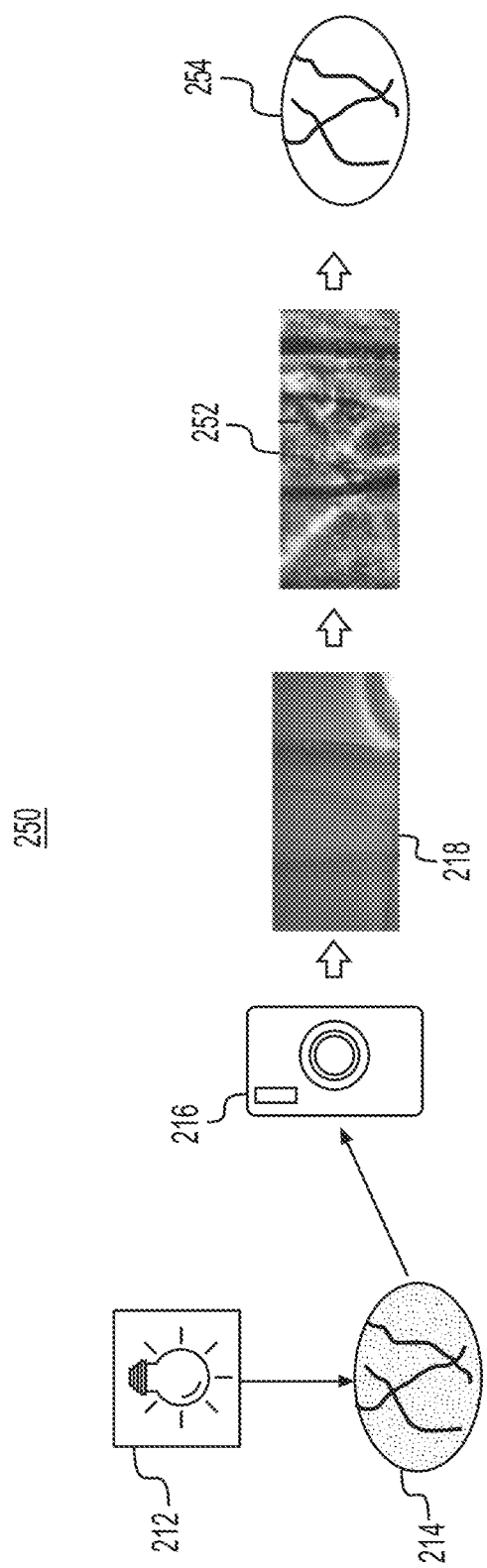

FIG. 2b shows a second image enhancement system 250. The second image enhancement system 250 shows the illumination source 212, the spectrum image 214, the spectral imager 216, and the pre-enhanced image 218, as described above in connection with FIG. 2a. FIG. 2b also shows an enhanced contrast image 252 and a final colorized image 254.

In the second image enhancement system 250 of FIG. 2b, the pre-enhanced image 218 is generated using similar techniques as described above in connection with FIG. 2a. After the pre-enhanced image 218 is generated, the system 250 applies a Histogram Contrast Enhancement (HCE) algorithm to further enhance the identified area of interest in the pre-enhanced image 218, thus generating the enhanced contrast image 252 (e.g., an HCE contrast image). In one example, the HCE algorithm may be a Contrast Limited Adaptive Histogram Equalization algorithm.

After the enhanced contrast image 252 is generated, spatial filters are applied to generate the final colorized image 254. In one example, the spatial filters applied in system 250 are the same or substantially similar as those applied in system 210.

Figure 2C:
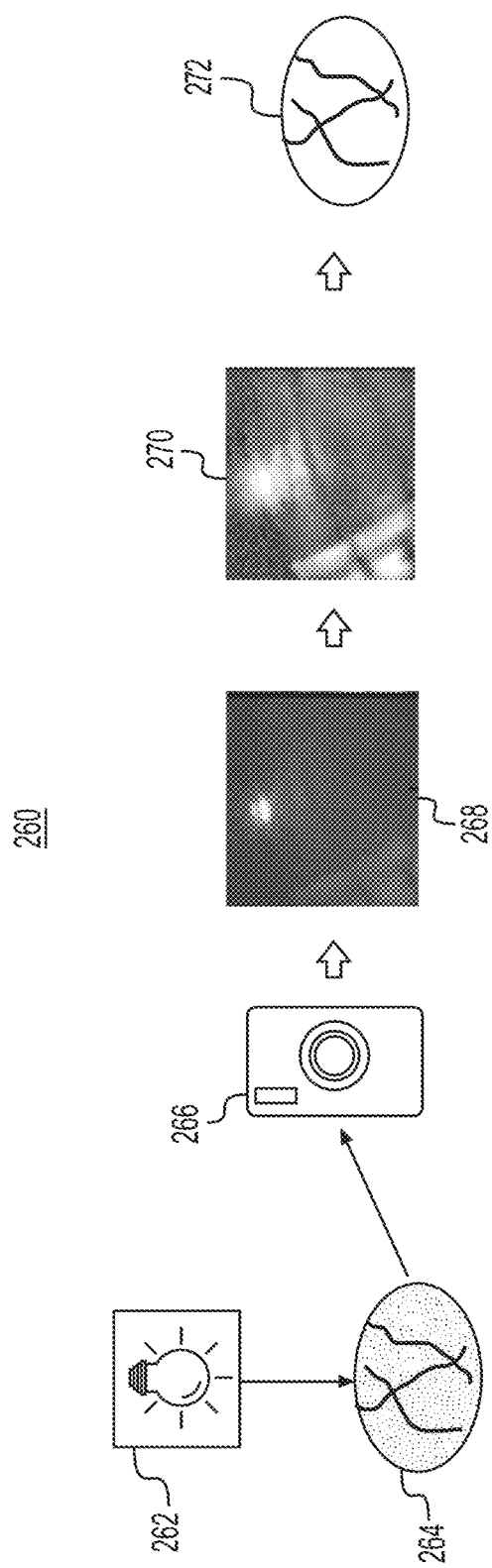

FIG. 2c shows a third image enhancement system 260. The third image enhancement system 260 shows a visible spectrum illumination source 262, a spectrum image 264, a red-green-blue (RGB) imager 266, a pre-enhanced image 268, an enhanced contrast image 270, and a final colorized image 272. The spectrum illumination source 262 is configured to project light in the visible wavelength spectrum onto a tissue area of interest of a patient via the endoscope 104 (e.g., via the one or more lumens described in connection with FIG. 1, above). In one example, the spectrum illumination source 262 is a balanced visible spectrum (RGB) illumination source with a balanced visible spectrum of light projected onto a tissue region.

In one example, a white light image with a balanced visible spectrum provides several benefits. It allows for standard RGB visualization as seen by the naked eye in most natural lighting. Additionally, digital filters or hyperspectral imagers may be used to post-process such images for improved contrasts, feature extractions, and/or other enhancements that may not be readily perceivable by the naked human eye. A full spectrum white balanced light provides all spectrums in an image that can later be processed with digital filters or specialty imagers such as a hyperspectral imager.

After the visible spectrum illumination source 262 emits light onto the tissue region of the patient, the imaging system 108 (described in FIG. 1) captures the spectrum image 264 (e.g., a visible spectrum image). The spectrum image 264 is similar to the spectrum image 214 described above. For example, the spectrum image 264 may represent upper GI bleeding captured by the visible spectrum illumination source 262. Similar to the spectrum image 214, a viewer of the spectrum image 264 may not be able to discern the blood vessels that are causing the bleed.

The RBG imager 266 is configured to apply a filter to the spectrum image 264 to generate a true color image of the area of interest, resulting in the pre-enhanced image 268. The pre-enhanced image 268 represents an actual RBG image of the area of interest, and identifies the bleeding vessels more clearly relative to the spectrum image 264. In one example, the RBG image represents a "natural" image with limited contrast and visibility of the vessels. This image can be used for application to an HCE algorithm directly without applying any other spectral filters. In one example, a red filter may be used to provide pre-enhancements which the HCE can use for higher contrast capabilities.

After the pre-enhanced image 268 is generated, an HCE filter is applied to the pre-enhanced image to generate an enhanced contrast image 270 (e.g., an HCE filter image). The enhanced contrast image 270 further colorizes the pre-enhanced image 268 in a higher contrast, and thus further enhances the view of the bleeding vessels. The spatial filter 272 operates similarly to those described in connection with FIGS. 2a and 2b to recolor the enhanced contrast image 270 and to generate the final colorized image 272 with the blood vessels defined in the image.

Figure 2D:
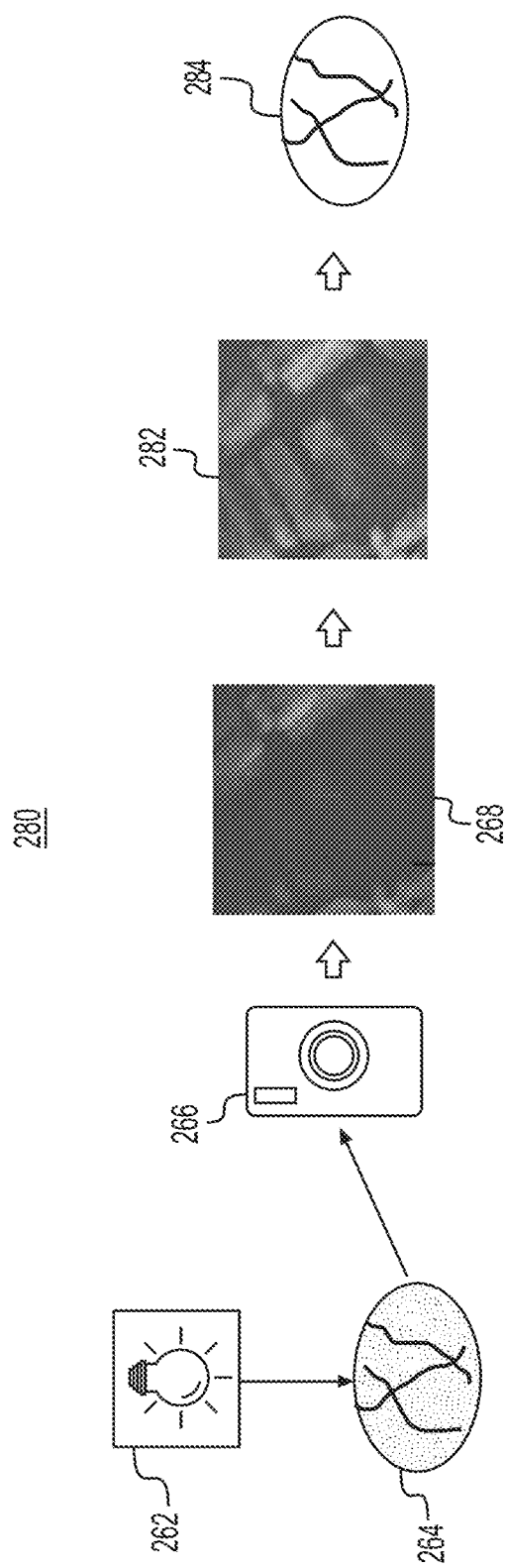

FIG. 2d shows a fourth image enhancement system 280. The fourth image enhancement system 280 has a visible spectrum illumination source 262, a spectrum image 264, an RGB imager 266, and a pre-enhanced image 268 as described above in connection with FIG. 2c. FIG. 2d also shows an enhanced contrast image 282 and a final colorized image 284.

In the fourth image enhancement system 280 of FIG. 2d, the pre-enhanced image 268 is generated using similar techniques as described above in connection with FIG. 2c. After the pre-enhanced image 268 is generated, the system 280 applies a red-balanced hue filter (R-filter) algorithm to convert the pre-enhanced image 268 to a grayscale image, generating the enhanced contrast image 282.

Figure 5D:
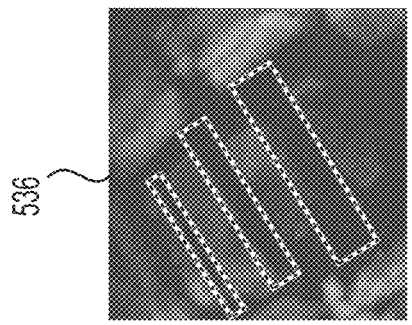
FIG. 5d shows further example images, according to exemplary aspects of the present disclosure.
Figure 5D:
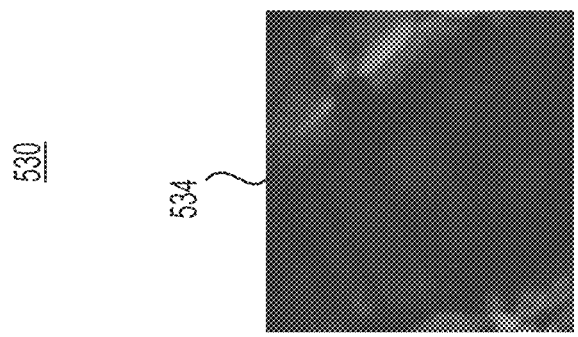
Figure 5D:
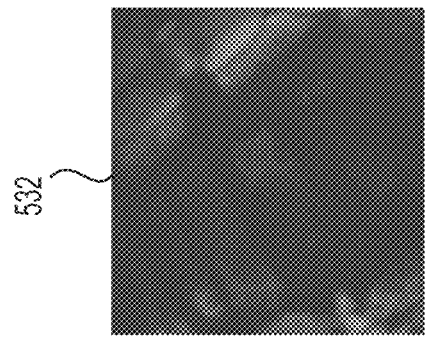

After the enhanced contrast image 282 is generated, spatial filters are applied to generate the final colorized image 284. In one example, the spatial filters applied in system 280 are the same or substantially similar as those applied in systems 210, 250, and 260. FIG. 5d shows example images 530 associated with the fourth image enhancement system 280. For example, the images 530 may include a first image 532 that is an original red-green-blue image, a second image 534 having a red (R) to gray scaled filter applied, and a third image 536 having a spatial filter applied.

Figure 3:
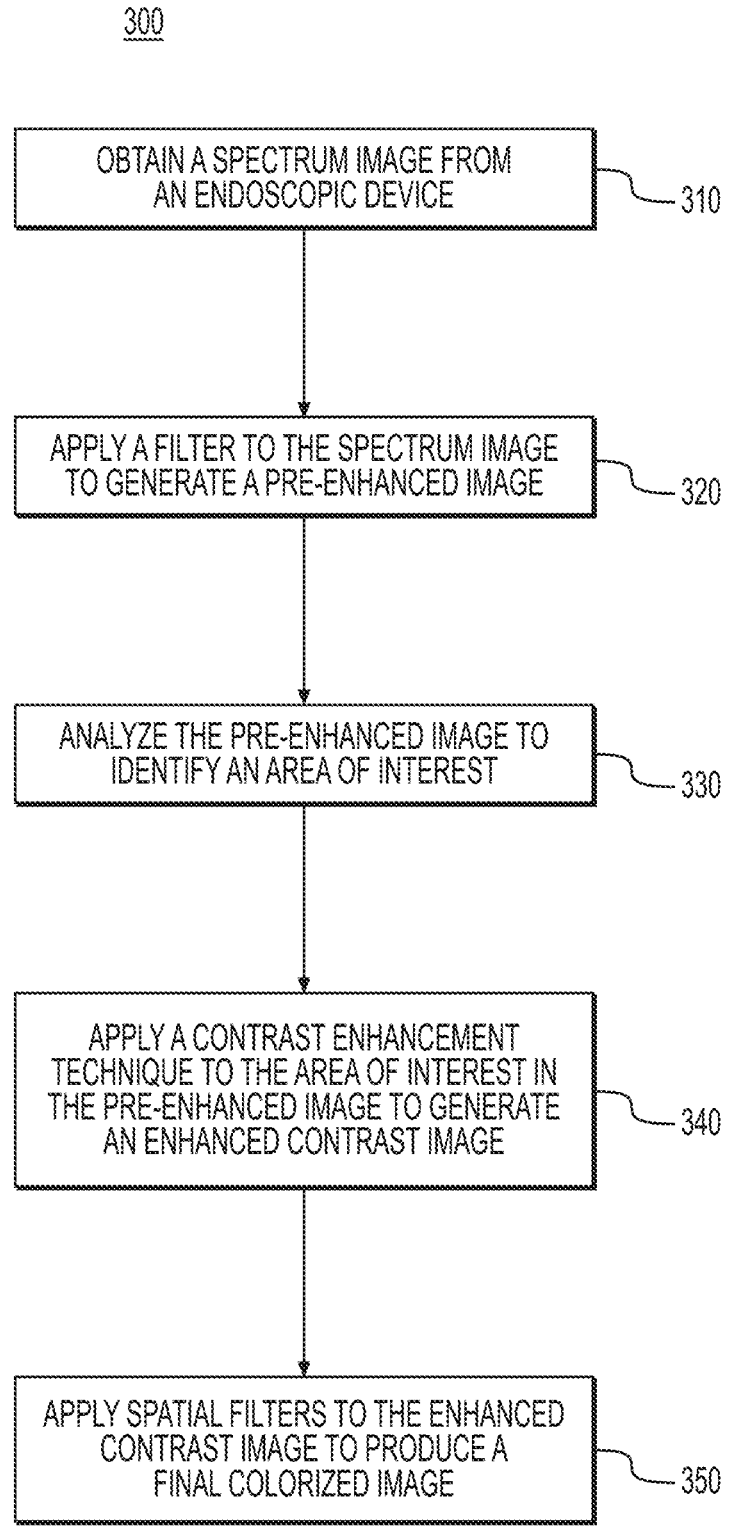
FIG. 3 illustrates a flow chart depicting operations for image enhancement techniques to identify bleeding vessels, according to exemplary aspects of the present disclosure.

Reference is now made to FIG. 3, which shows an example flow chart 300 depicting operations for image enhancement techniques to identify bleeding vessels. The operations of the flowchart may be stored in the image enhancement logic 109 of the image processing device 105. In one example, a processor of the image processing device 105 is configured to execute the image enhancement logic 109 to perform the operations described herein.

At reference numeral 310, a spectrum image is obtained from an endoscopic device. The spectrum image is of bleeding in a patient, for example, in an upper GI area of the patient. At 320, a filter is applied to the spectrum image to generate a pre-enhanced image. The filter enhances the spectrum image at one or more light wavelengths in the light spectrum. At 330, the pre-enhanced image is analyzed to identify an area of interest. The area of interest represents a portion of the upper GI area with an active bleed. At 340, a contrast enhancement technique is applied to the area of interest in the pre-enhanced image to generate an enhanced contrast image. At 350, spatial filters are utilized to the enhanced contrast image to produce a final colorized image with defined blood vessels of the GI area of the patient.

It should be appreciated that all of the techniques described herein may occur during real time imaging of a patient. For example, the image processing and enhancement techniques described herein may occur while an image is being captured by the endoscope 104 and the image processing device 105. Thus, the techniques described herein may represent real time processing for treatment of an active bleed in circumstances where it is difficult for a viewer to visualize or capture an image of blood vessels needed for treatment. In another alternative, the techniques described herein may occur during post-processing, after an image is collected from the patient.

Figure 4:
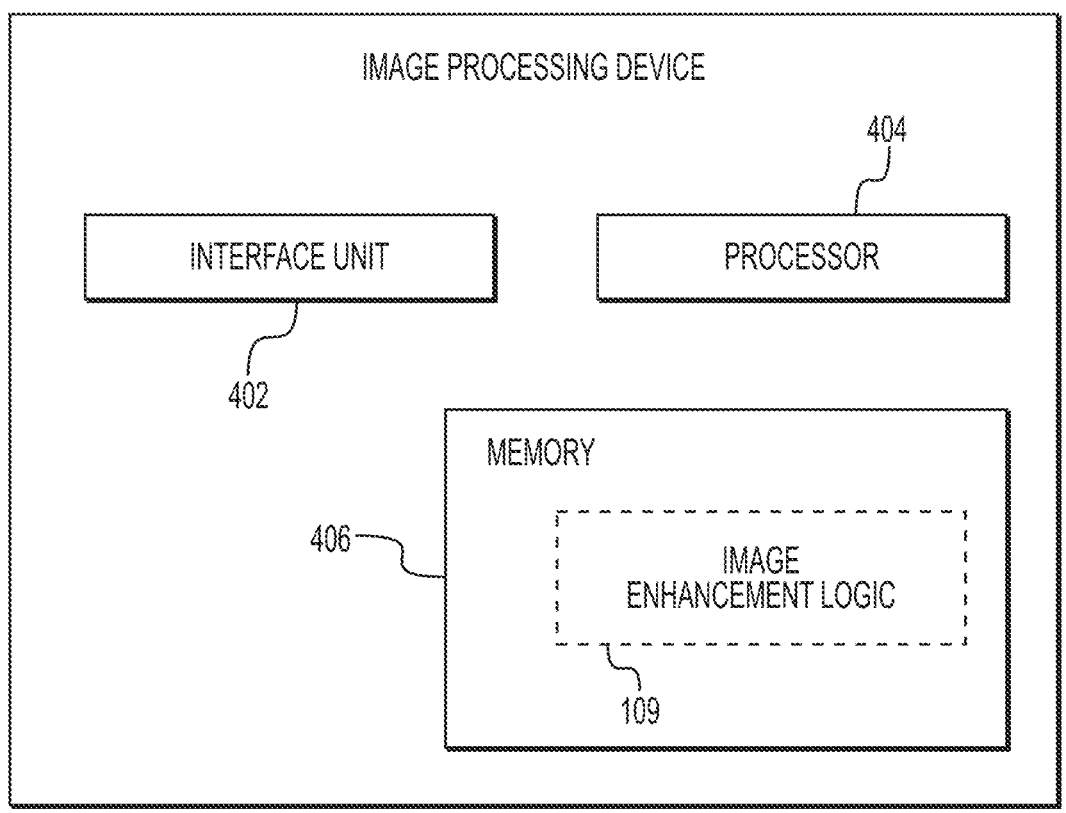
FIG. 4 shows an example block diagram of a computing device configured to perform image enhancement techniques to identify bleeding vessels, according to exemplary aspects of the present disclosure.

FIG. 4 is a simplified functional block diagram of the image processing device 105, described in connection with FIG. 1, above. It should be appreciated that the image processing device 105 may be any computing device. The image processing device 105 shows an interface unit 402, a processor 404, and a memory 406. The memory 406 includes image enhancement logic 109 configured to perform the image enhancement techniques, e.g., to identify bleeding vessels in an active upper GI bleeding event, as described by the techniques herein. The image processing device 105 also may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed systems, methods, and/or graphical user interfaces may be executed by or implemented by a computing system consistent with or similar to the descriptions herein. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

It should be understood that one or more of the aspects of any of the medical devices described herein may be using in combination with any other medical device known in the art, such as medical imaging systems or other scopes such as colonoscopes, bronchoscopes, ureteroscopes, duodenoscopes, etc., or other types of imagers.

It also should also be understood that one or more aspects of any of the medical devices described herein may be used for sensing, monitoring, or ablating tissue in any part of the human body. For example any of the medical devices described herein may be used in medical procedures such as for endoscopic cholangio-pancreatography, colonoscopies, cancer screening, examination of mucinous lesions, and/or other procedures where removal and/or detection of the type of tissue is needed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for enhancing medical images, the method comprising:
   at a processor device in communication with an endoscopic device, obtaining from the endoscopic device a spectrum image of bleeding in an upper gastrointestinal (GI) area of a patient;
   at the processor device, applying a filter to the spectrum image to generate a pre-enhanced image, wherein the filter enhances the spectrum image at one or more light wavelengths in the light spectrum, and the pre-enhanced image includes three spectral filters at 490 nm, 630 nm, and 640 nm;
   analyzing the pre-enhanced image to identify an area of interest, wherein the area of interest represents a portion of the upper GI area with an active bleed;
   applying a contrast enhancement technique to the area of interest in the pre-enhanced image to generate an enhanced contrast image; and
   applying spatial filters to the enhanced contrast image to produce a final colorized image with defined blood vessels in the upper GI area of the patient.

2. The method of claim 1, wherein applying the filter to the spectrum image comprises applying the filter to the spectrum image at a light wavelength at which a light absorption rate of oxygenated hemoglobin differs from a light absorption rate of deoxygenated hemoglobin.

3. The method of claim 1, wherein applying the filter to the spectrum image comprises applying the filter to the spectrum image using a red-green-blue (RGB) color filter.

4. The method of claim 1, wherein applying the contrast enhancement technique comprises applying a histogram contrast algorithm to the area of interest.

5. The method of claim 1, wherein the pre-enhanced image is a false color image.

6. The method of claim 1, wherein applying the filter to the spectrum image comprises applying the filter to the spectrum image to generate the pre-enhanced image with the area of interest more visually enhanced than the spectrum image.

7. The method of claim 1, wherein applying the contrast enhancement technique comprises applying the contrast enhancement technique to the area of interest to generate the enhanced contrast image with the area of interest more visually enhanced than the pre-enhanced image.

8. The method of claim 1, wherein applying the spatial filters to the enhanced contrast image comprises applying the spatial filters to the enhanced contrast image to produce the final colorized image that represents a recolorization of the enhanced contrast image.

9. The method of claim 1, wherein applying the contrast enhancement technique comprises applying the contrast enhancement technique during real time imaging of the patient.

10. The method of claim 1, wherein applying the contrast enhancement technique comprises applying the contrast enhancement technique during post-processing after the spectrum image is obtained from the patient.

11. The method of claim 1, wherein analyzing the pre-enhanced image comprises analyzing the pre-enhanced image to identify the area of interest that is a narrow field of visualization of the pre-enhanced image.

12. A non-transitory computer readable medium storing instructions that, when executed by one or more processors of a computer system, cause the one or more processors to perform operations comprising:
    obtaining from an endoscopic device a spectrum image of bleeding in an upper gastrointestinal (GI) area of a patient;
    applying a filter to the spectrum image to generate a pre-enhanced image, wherein the filter enhances the spectrum image at one or more light wavelengths in the light spectrum, and the pre-enhanced image includes three spectral filters at 490 nm, 630 nm, and 640 nm;
    analyzing the pre-enhanced image to identify an area of interest, wherein the area of interest represents a portion of the upper GI area with an active bleed;
    applying a contrast enhancement technique to the area of interest in the pre-enhanced image to generate an enhanced contrast image, and
    applying spatial filters to the enhanced contrast image to produce a final colorized image with defined blood vessels in the upper GI area of the patient.

13. The computer readable medium of claim 12, wherein applying the filter to the spectrum image comprises applying the filter to the spectrum image at a light wavelength at which a light absorption rate of oxygenated hemoglobin differs from a light absorption rate of deoxygenated hemoglobin.

14. The computer readable medium of claim 12, wherein applying the contrast enhancement technique comprises applying a histogram contrast algorithm to the area of interest.

15. A computer device for enhancing medical images, the computer device comprising:
    an interface unit;
    a memory storing instructions; and
    one or more processors configured to perform operations including:
        obtaining from an endoscopic device a spectrum image of bleeding in an upper gastrointestinal (GI) area of a patient;
        applying a filter to the spectrum image to generate a pre-enhanced image, wherein the filter enhances the spectrum image at one or more light wavelengths in the light spectrum, and the pre-enhanced image is a false color image with three spectral filters at 490 nm, 630 nm, and 640 nm;
        analyzing the pre-enhanced image to identify an area of interest, wherein the area of interest represents a portion of the upper GI area with an active bleed;
        applying a contrast enhancement technique to the area of interest in the pre-enhanced image to generate an enhanced contrast image; and
        applying spatial filters to the enhanced contrast image to produce a final colorized image with defined blood vessels in the upper GI area of the patient.

16. The computer device of claim 15, wherein applying the filter to the spectrum image comprises applying the filter to the spectrum image at a light wavelength at which a light absorption rate of oxygenated hemoglobin differs from a light absorption rate of deoxygenated hemoglobin.

17. The computer device of claim 15, wherein applying the contrast enhancement technique comprises applying a histogram contrast algorithm.

* * * * *